US006603554B1

(12) United States Patent
Eisenberg et al.

(10) Patent No.: US 6,603,554 B1
(45) Date of Patent: Aug. 5, 2003

(54) APPARATUS AND METHOD TO MEASURE LIGHT ATTENUATION THROUGH A WINDOW

(75) Inventors: Eric C. Eisenberg, Redmond, WA (US); Shaun C. Hampton, Klamath Falls, OR (US); Jeffrey C. Adams, Seattle, WA (US); David P. Bajorins, Redmond, WA (US)

(73) Assignee: Terabeam Corporation, Kirkland, WA (US)

( * ) Notice: Subject to any disclaimer, the term of this patent is extended or adjusted under 35 U.S.C. 154(b) by 331 days.

(21) Appl. No.: 09/746,122

(22) Filed: Dec. 22, 2000

(51) Int. Cl.[7] .................................................. G01N 11/59

(52) U.S. Cl. ...................................... 356/434; 356/239.1

(58) Field of Search ................................ 356/432, 433, 356/434, 435, 440, 239.1

(56) References Cited

U.S. PATENT DOCUMENTS

| 4,730,932 A | * | 3/1988 | Iga et al. ..................... 356/432 |
| 4,925,310 A | * | 5/1990 | Feppon et al. ............... 356/434 |
| 6,084,662 A | * | 7/2000 | Seaburn ........................ 356/73 |
| 6,118,526 A | | 9/2000 | Hidalgo et al. .............. 356/239 |

* cited by examiner

Primary Examiner—Richard A. Rosenberger
(74) Attorney, Agent, or Firm—Blakely Sokoloff Taylor & Zafman, LLP

(57) ABSTRACT

An apparatus and method determines light transmission through a window. The window may be a single-pane or a double-pane window, and may or may not have coatings on its interior/exterior surfaces. Light transmission through the window can be measured based on power levels of light incident on the window and light reflected from the window. Such measurements can be performed for a wireless optical telecommunication system, in situations where it may be difficult or impossible to access both sides of a window to place or retrieve measurement equipment.

20 Claims, 4 Drawing Sheets

APPARATUS AND METHOD TO MEASURE LIGHT ATTENUATION THROUGH A WINDOW

BACKGROUND OF THE INVENTION

1. Field of the Invention

The present invention relates generally to optics and the transmission of light, and in particular but not exclusively, relates to the measurement of light attenuation through a window.

2. Background Information

Window design is an important consideration in the architectural planning of a building. In addition to affecting the temperatures within the building's interior spaces, the size and number of windows influence the aesthetic appearance of the building. Indeed, many skyscrapers in crowded urban environments are identifiable by large multi-colored panes of glass that make up the skyscrapers' siding.

To help keep such buildings cool during hot sunny days, the panes of glass and the windows are typically tinted or coated with a reflective material. The reflective coating acts to reflect some of the sun's incident light rays, while the tinting acts to absorb or filter certain wavelengths. That is, depending on the type of material used, some windows can be very opaque at certain wavelengths. By reflecting or filtering some of the sun's incident light rays, the amount of energy used to cool the building during the summer can thus be reduced, thereby resulting in more efficient operation and maintenance.

Measurement of light attenuation through an existing or installed window to determine the window's reflectiveness or absorption is particularly difficult. One technique is to place a photodetector on one side of an installed window (e.g., on one side of its glass pane), sending light through the glass pane from the other side, and then using the photodetector to measure the amount of light that passes through the glass pane.

Such a technique is impractical for a number of reasons. Most pre-existing or installed windows, particularly those in skyscrapers, are difficult to reach/access because of the skyscraper's height, and also cannot be opened to install/retrieve the light-measuring equipment. Thus, measurement of light attenuation through an installed window is most easily taken at ground-level windows, which are not always made of the same material as windows at higher levels of the skyscraper, and thus this technique does not provide an accurate determination of light attenuation performance of all windows as a whole.

A second technique is to measure and compare ambient light, which is a technique that is less accurate than the first technique described above. With the second technique, a photodetector having a filter (such as a bandpass filter) in front of it is placed adjacent to the interior side of the window at a specific angle. The photodetector-filter is then taken outside as fast as possible and held at the same angle. The difference in measured light is subsequently compared to obtain a very rough approximation of light attenuation through the window.

As with the first technique, the second technique is very impractical and inaccurate. The photodetector-filter unit needs to be held at the same angle at both sides of the window, which is itself difficult to do in an exact way. More significantly, it is impractical to use this technique for a skyscraper's installed windows that do not open, since a person performing the measurement has to "dash" from an upper floor of the skyscraper after taking the interior measurement, to the outside of the skyscraper to obtain an exterior measurement at ground level. The time taken to obtain the measurement from the outside of the skyscraper reduces the accuracy of this technique.

Accordingly, improvements are needed in the measurement of light attenuation through a window.

SUMMARY OF THE INVENTION

An aspect of the invention obtains a first value indicative of a power level of a first light signal incident on a window. A second value indicative of a power level of a second light signal reflected from a first surface of the window is obtained. A third value indicative of a power level of a third light signal reflected from a second surface of the window is obtained. A fourth value indicative of light transmission through the window is determined based on the obtained first, second, and third values.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE ILLUSTRATED EMBODIMENTS

Embodiments of an apparatus and method to measure light attenuation through a window are described herein. In the following description, some specific details are given to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As an overview, an embodiment of the invention measures light transmission through a window, such as a window that may be made from a translucent material, such as a glass material. An embodiment of the invention can be used to measure light attenuation through other translucent or semi-translucent material, including but not limited to, plastic material, silicon material that is translucent at certain wavelengths (the mid-infrared wavelength range, for example), and the like. The window may be a single-pane or a double-pane window or may have any number of panes, and may or may not have coatings on its interior/exterior surfaces. In accordance with an embodiment of the invention, light transmission through the window is measured based on power levels of light incident on the window and light reflected from the window. Light transmission can be measured in situations where it is difficult or impossible to place a detector on the other side of the window from a light source.

An embodiment of the invention may have applications in a freespace or wireless optical telecommunication system. Such a wireless optical telecommunication system can use laser light or other type of light signal to communicate between transceivers. In some situations, such transceivers may be positioned behind windows that may attenuate or otherwise affect the level of light that passes through the window, such as via reflection or absorption. Thus, for efficient and effective optical communication, the amount of light that is transmitted through a window needs to be known so that the transmitters, receivers, and/or transceivers can be optimally calibrated or adjusted.

Figure 1:
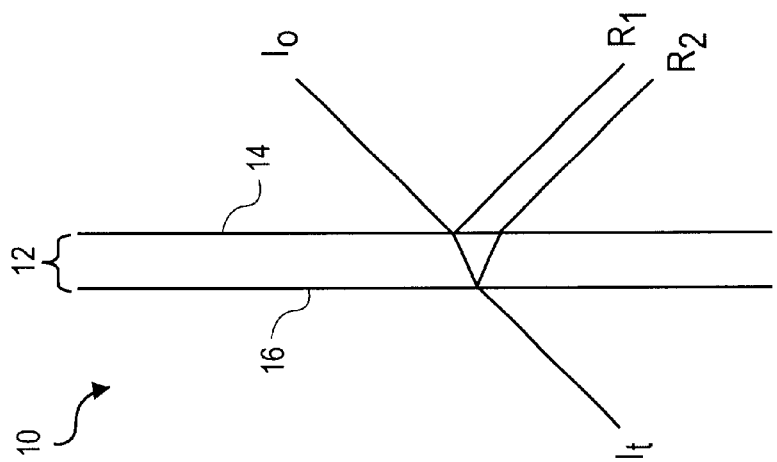
FIG. 1 illustrates an example of reflection and transmission through a single-pane window.

FIG. 1 illustrates an example of light reflection and transmission through a window 10. The window 10 typically comprises a glass pane 12 that may or may not have tinting or other additives mixed into it. The glass pane 12 has a first surface 14 and a second surface 16. If the window 10 is already installed in a building, the first surface 14 can be the interior surface that faces a room of the building, and the second surface 16 can be the exterior surface that faces the outside of the building.

In actual operation of a wireless optical telecommunication system, a light signal is incident on the second surface 16, and a transceiver is positioned behind the first surface 14 to receive the light that is transmitted through the glass pane 12. Similarly, the transceiver positioned behind the first surface 14 can send a light signal incident against the first surface 14, which then passes through the glass pane 12 and out from the second surface 16. For purposes of illustrating an operation of an embodiment of the invention, a description in the context of a light signal incident against the first surface 14 will be provided herein, and it is understood that principles of the invention are applicable regardless of which side the light signal is coming from.

In FIG. 1, a light signal having a power level $I_0$ (an optical intensity in watts) is incident against the first surface 14. A first reflected light signal having a power level $R_1$ (an optical intensity in watts) is reflected off the first surface 14. Meanwhile, the light signal propagates through the glass pane 12 (from right to left) and is reflected off the second surface 16 (e.g., a back reflection within the glass material 12 from left to right), resulting in a second reflected light signal having a power level $R_2$ that comes off the first surface 14.

An example equation that can be used to relate the power level $I_0$ to a power level $I_t$ of a light signal that eventually leaves the glass pane 12 from the second surface 16 can be described by the following:

$$\frac{I_t}{I_0} = \frac{\sqrt{R_2}}{\sqrt{R_1}} - \frac{\sqrt{R_2 R_1}}{I_0} \quad (1)$$

In Equation (1), the quantity $I_t/I_0$ can be referred to as a transmittance T, which represents a percentage of light that makes it from before the first surface 14 to after the second surface 16 of the window 10. The light attenuation or loss through the window 10 can be calculated in decibels according to the formula Loss=−10 * log (T).

Equation (1) may be applicable for typical situations where both surfaces 14 and 16 have the same index of refraction. Because surfaces of most insulated glass units (IGUs) are uncoated, it can be assumed that the same ratio of light is reflected off the second surface 16 as the first surface 14. It is to be appreciated that Equation (1) can also be applied where both surfaces 14 and 16 are coated with the same coating. In an embodiment, the light signal can be a laser light signal having a wavelength of approximately 1548 nm. It is also to be appreciated that Equation (1) may be applied to any wavelength of light.

Figure 2:
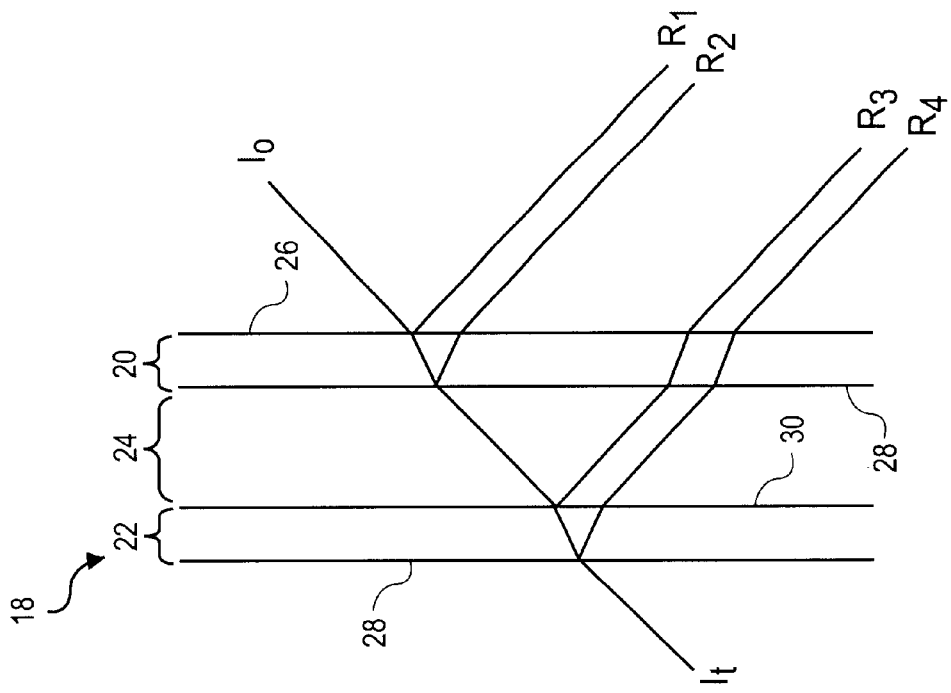
FIG. 2 illustrates an example of reflection and transmission through a double-pane window.

FIG. 2 illustrates an example of reflection and transmission through a double-pane window 18. The window 18 comprises two panes 20 and 22 of glass material, separated by an air gap 24. As shown in FIG. 2, a light signal having a power level of $I_0$ is incident against a first surface 26 of the pane 20, and a light signal having a power level $I_t$ passes from a second surface 28 of the pane 22.

A first reflected light signal having a power level $R_1$ is reflected off the first surface 26 of the pane 20. A second reflected light signal having a power level $R_2$ is reflected off a third surface 28 as the incident light signal travels within the pane 20. The incident light signal continues on to propagate through the air gap 24 from right to left until it is reflected off a fourth surface 30 of the pane 22. That reflected light propagates (from left to right through the air gap 24 and the pane 20), until a third reflected light signal having a power level $R_3$ exits from the first surface 26. Meanwhile, the incident light signal continues to propagate within the pane 22 until it is reflected off the second surface 28. This reflected light propagates (from left to right through the pane 22, the air gap 24, and the pane 20), until a fourth reflected light signal having a power level $R_4$ exits from the first surface 26 of the pane 20.

An example equation that can be used for the transmittance $T=I_t/I_0$ in the situation of FIG. 2 can be described by the following:

$$\frac{I_t}{I_0} = \frac{\sqrt{R_4}}{\sqrt{R_1}} - \frac{\sqrt{R_4 R_1}}{I_0} \quad (2)$$

As with Equation (1), Equation (2) can be applied in situations where the surfaces 26 and 28 have the same index of refraction (e.g., both are uncoated or both are coated with the same coating). Equation (2) is also applicable in situations where the interior surfaces 28 and 30 may have the same or different indexes of refraction, due to the presence/absence of the same or different coatings. This characteristic is represented in Equation (2), where the values $R_2$ and $R_3$ of the light signals reflected from the interior surfaces 28 and 30, respectively, do not influence the transmittance T. Surface coatings, if present, are typically on the interior surfaces 28 and 30 in many situations.

Furthermore, Equations (1) and (2) also implicitly take into account any absorption of light power by the windows 12 or 18. That is, the measured power levels R2 or R4 are both already influenced by absorption (if any) by the time they are measured, since their corresponding light signals have propagated through the window material (e.g., absorptive regions) multiple times.

Figure 3:
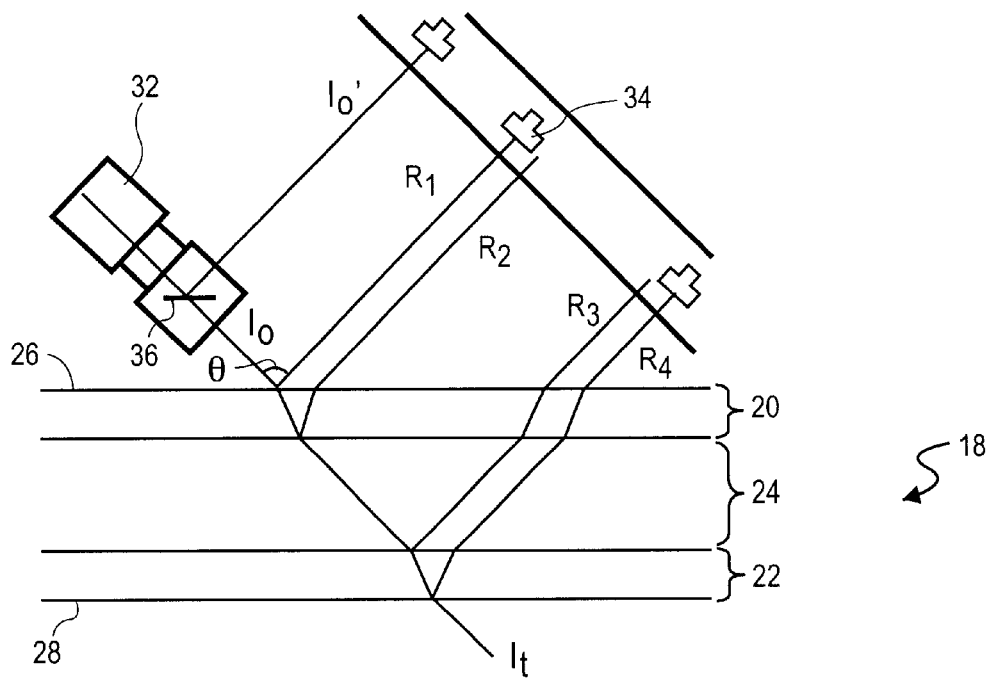
FIGS. 3 and 4 illustrate an example operation of an embodiment of the invention based on light reflection and transmission through the window panes of FIG. 1 or FIG. 2.

Therefore, as illustrated in FIGS. 1 and 2, the power level $I_t$ of transmitted light, which is indicative of the level of attenuation through a window, can be determined by reading (and comparing) the power level of light reflected off the front and rear surfaces of a window (e.g., $R_1$ and $R_2$, or $R_1$ and $R_4$) and the power level $I_0$ of the incident light signal. FIG. 3 illustrates an example operation of an embodiment of the invention based on light reflection and transmission through a window, such as the windows shown in FIG. 1 or 2.

A light source 32, such as a laser light source, directs the incident light signal having the power level $I_0$ against the first surface 26 of the pane 20. A photodetector 34 (such as a photodiode, phototransistor, PIN detector, charge-coupled device, or other detector) detects a power level $I_0'$ that is split off the incident light signal having a power level $I_0$ by a beamsplitter 36, and also detects the power levels $R_1$ and $R_4$ of the reflected light signals.

In an embodiment, the value of $I_0'$ is 10 percent, for example, of the value of $I_0$. That is, 10 percent of the incident light signal is split off by the beamsplitter 36 and directed to the photodetector 34. Thus for Equations (1) or (2), the value of $I_0$ indicated in the denominator on the right hand side of the equation(s) can be replaced by $9 * I_0'$, so as to obtain a value for $I_0$ that is actually incident against the first surface 26 (or the first surface 14).

In an embodiment, a single photodetector 34 can be used to detect the light, with the photodetector 34 capable of being moved to different positions to detect the power level of each individual light signal. In another embodiment, multiple photodetectors at different positions can be used. Furthermore, while FIG. 3 shows an embodiment where the power level $I_0'$ is detected as a light signal that is split off from the main incident light signal, it is possible to provide an embodiment where the power level $I_0$ is detected directly without use of the beamsplitter 36. For example, this may be done by directly pointing the output of the light source 32 towards the photodetector 34 prior to pointing the light source 32 towards the first surface 26, or by reading a meter of the light source 32 that indicates the output power level $I_0$.

In an embodiment, the light source 32 is oriented such that an angle θ between the incident light signal and the first reflected light signal is approximately 90 degrees. The exact value of the angle θ may vary from one situation to another. In general, the orientation of the light source 32 is chosen such that there is sufficient separation between the light signals and such that the power levels of the light signals are not unrealistically attenuated. For instance, if the angle θ is 0 degrees (e.g., the light source 32 is aimed directly perpendicular to the first surface 26), then there is minimal or no separation between the reflected light signals. Conversely at the other extreme, if the angle θ is too large (e.g., significantly over 90 degrees), then there is significant separation between the reflected light signals but high attenuation.

Figure 4:
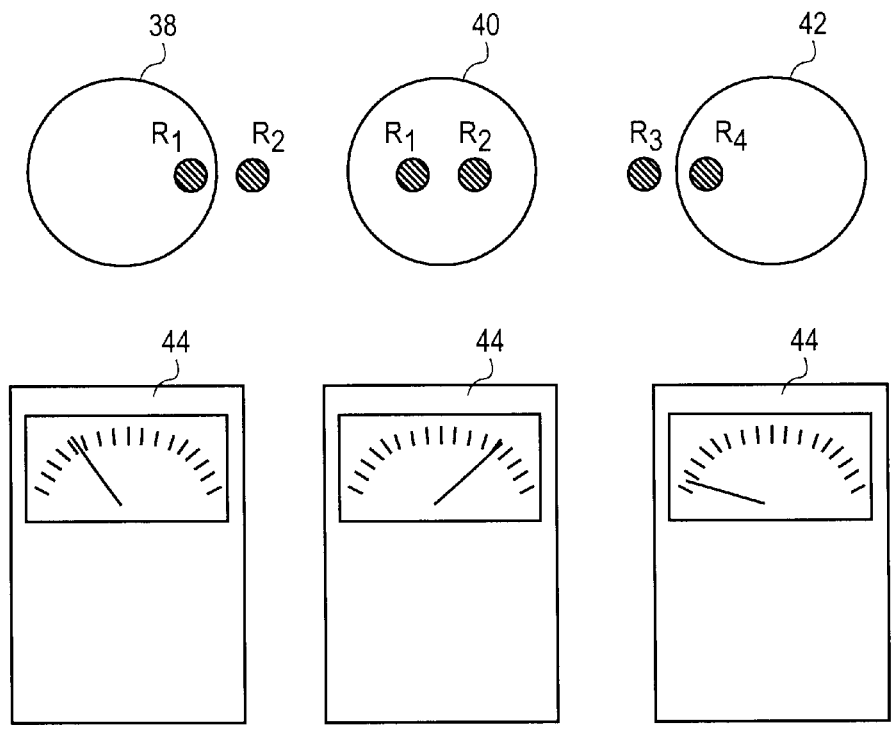

FIG. 4 further illustrates the operation depicted in FIG. 3 as a sequence of readings 38–42 as the photodetector 34 is moved to detect the reflected light signals. The various power levels of the reflected (and incident) light signals may be displayed by a meter unit 44 in one embodiment. In another embodiment, the meter unit 44 can display the transmittance T, or the power level $I_t$ of the transmitted light signal or other values, based on a determination or calculation shown in Equations (1) or (2).

At the reading 38, the photodetector 34 is positioned such that the proper one of two reflected light signals is measured or detected. That is, the power levels $R_1$ and $R_2$ of the first set of reflected light signals typically appear as a pair of power peaks, sometimes spaced closely together as depicted at the reading 38 in FIG. 4. Thus, the first detected power peak is known to correspond to the power level $R_1$ and is measured, while movement of the photodetector 34 a short distance thereafter will detect the power level $R_2$.

At the reading 40, both the power levels $R_1$ and $R_2$ are detected at the same time by the photodetector 34 (if the photodetector 34 is moved too far to the right of the peak power reading that corresponds to $R_1$). In an embodiment, this results in an abnormally high power reading from the meter unit 44, which indicates to the user that two power levels may have been measured. In such a situation, the user can discard the reading at 40, and move the photodetector 34 back (to the left) to obtain a proper reading at 38 for $R_1$.

The reading at 42 illustrates detection of a peak power corresponding to the power level $R_4$. As before, two peak power levels $R_3$ and $R_4$ are present and may be spaced closely together. The second of the two peak power levels corresponding to $R_4$ is detected, and the peak power level corresponding to $R_3$ can be discarded.

Figure 5:
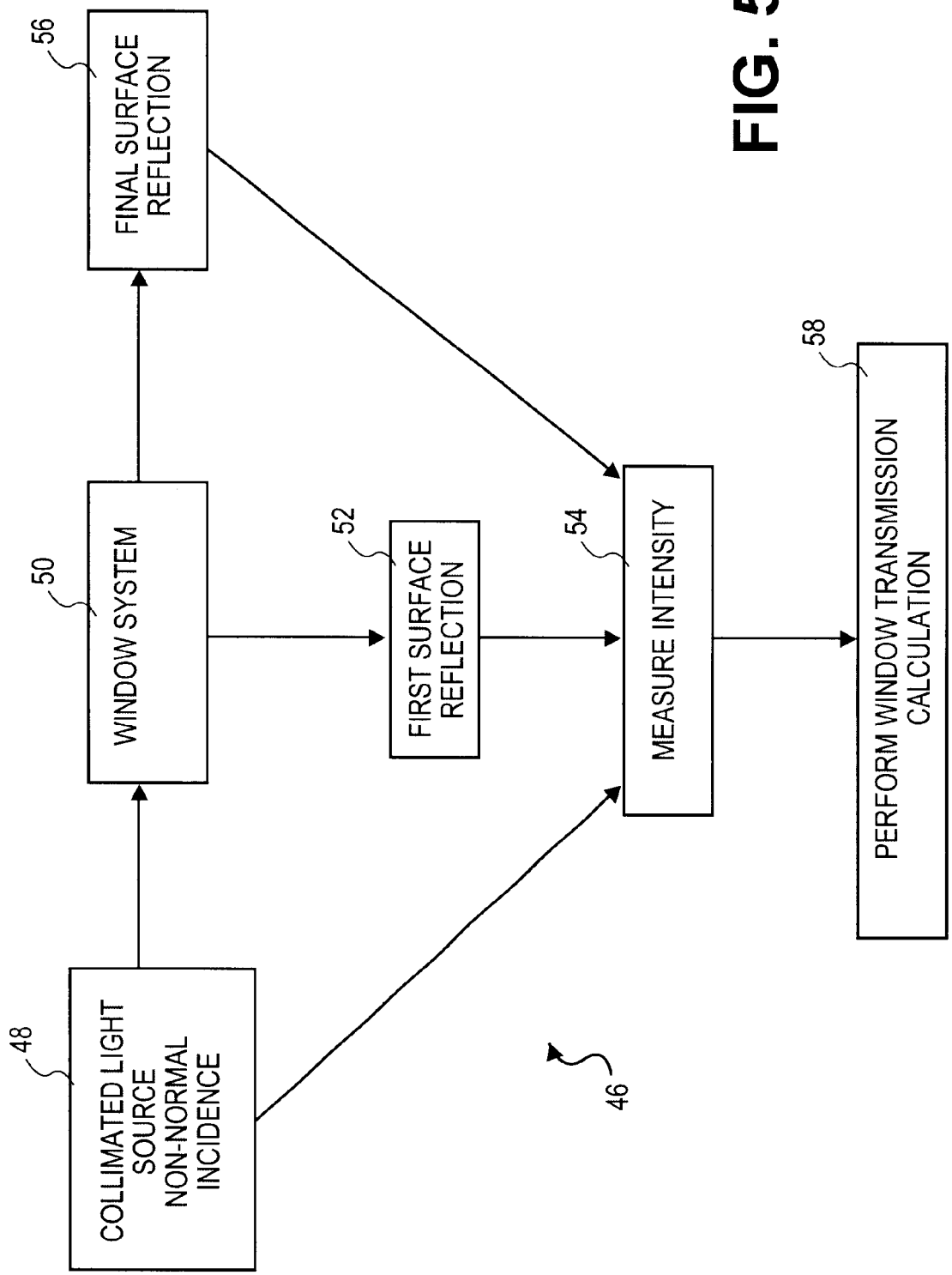
FIG. 5 is a flowchart further depicting the operations shown in FIGS. 3 and 4.

FIG. 5 is a flow diagram 46 that further illustrates a sequence of events in connection with determination of light attenuation through a window, according to operations such as those depicted in FIGS. 3 and 4. Beginning at blocks 48 and 50, a collimated light signal (such as a laser light signal from the light source 32) is directed with non-normal incidence at the window system (e.g., at the windows 10 or 18). At the same time or before, the intensity or power level of the incident light signal is measured at a block 54. A reflection off the first surface 26 (or the first surface 14) results at a block 52.

Next at the block 54, the intensity or power level of the first reflected light signal is measured, based on reflected light that is detected by the photodetector 34. This value is then stored or otherwise saved for later use. The photodetector 34 is moved until a reflection off the final or second surface 28 (or the second surface 16) results at a block 56. The intensity or power level of this second reflected light signal is measured at the block 54. Subsequently, window transmission calculation is performed at a block 58 to determine the transmittance T and/or the level of window attenuation. The calculation at the block 58 may be performed in several ways, including manually or automatically via software, as will be described later below.

Figure 6:
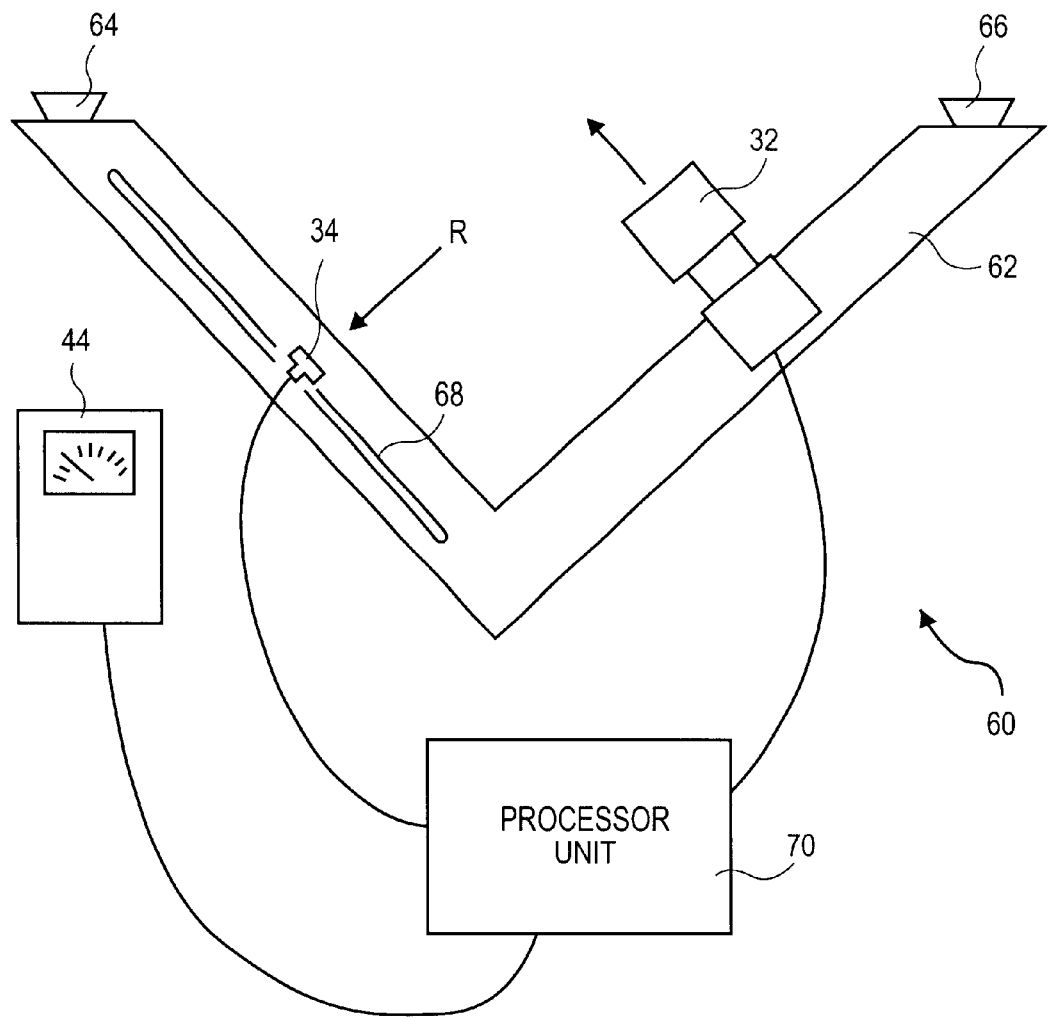
FIG. 6 is a diagram of an embodiment of an apparatus that can be used to perform the operations shown in FIGS. 3–5.

FIG. 6 is a block diagram of an embodiment of an apparatus 60 that can be used to perform light attenuation measurement operations, such as those depicted in FIGS. 3 5. The light source 32 and the photodetector 34 can be mounted or attached to a mount 62. The mount 62 can be attached to window surfaces 14 or 26 via suction cups 64 and 66, and it is to be appreciated that other attachment techniques may be used. The window can be an installed and/or not-opening window. The mount 62 includes a railing 68 or other mechanism to allow movement of the photodetector 34 to measure the various light signals corresponding to $I_0 B$, $R_1$, and $R_2$ or $R_4$.

According to an embodiment, the photodetector 34 and/or the light source 32 can be coupled to the meter unit 44. That is, the meter unit 44 provides/displays an output that corresponds to the power level(s) detected by the photodetector 34. Thereafter, a manual calculation can be performed by the user in an embodiment, using Equations (1) or (2) for example, to determine light attenuation and/or the transmittance T.

In another embodiment, outputs of the photodetector 34 and/or the light source 32 can be coupled to a processor unit 70. The processor unit 70 can include software or other machine-readable instructions stored on a machine-readable medium that performs the calculations according to Equations (1) or (2). The machine-readable medium can comprise RAM, ROM, a floppy disk, hard disk, CD, etc. Using the software, the processor unit 70 can output values representing any of the variables depicted in Equations (1) or (2). In another embodiment, the processor unit 70 can use look-up tables, instead of or in addition to performing calculations according to Equations (1) or (2), to provide values for the transmittance T or the power level $I_t$, based on a correlation or comparison between detected power levels and power levels stored in the lookup table(s).

The processor unit 70, in one embodiment, can also perform adjustment of values as a result of factors that may cause abnormal readings by the photodetector 34. Such factors can include back reflections within the glass due to presence of reflective coating for the window 18. Such adjustment may be done by the processor unit 70 using lookup tables in one embodiment, or by further calculation. In another embodiment, this adjustment may be performed through manual calculation.

The table below identifies adjustment values that can be used in one embodiment of the invention. It is understood that these values are merely illustrative of one embodiment, and that the values may change from one situation to another.

| Strongest reflection is about: | Divide from $R_4$ |
| --- | --- |
| 5 times bigger than $I_0'$ | 1.25 |
| 7 times bigger than $I_0'$ | 3 |
| 8 times bigger than $I_0'$ | 5 |
| 9 times bigger than $I_0'$ | 9 |

In conclusion, an embodiment determines light attenuation and/or light transmission through a window based on the incident light signal and reflected light signals. The light attenuation (and/or light transmission) can be determined based on Formulas/equations in one embodiment that relate a power level of the incident light signal to power levels of the reflected light signals. An embodiment of the invention is useful in situations where a window has already been installed, does not open, or is otherwise difficult to access from both sides.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize.

For example, while an embodiment of the invention can utilize Equations (1) or (2) to perform calculations, it is to be appreciated that another embodiment can be based on different equations or variations thereof. For instance, other equations can be derived based on different indices of refraction, number of panes present, etc. Furthermore, single-pane and double-pane windows are used herein for illustrative purposes. Equations can be derived, and/or attenuation measurement techniques based on the above-described embodiments can be used, for implementations where a window may have any number of panes, such as multiple-pane windows where the reflectivity at both the front and rear surfaces are the same.

These modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A method, comprising:
    obtaining a first value indicative of a power level of a first light signal incident on a window;
    obtaining a second value indicative of a power level of a second light signal reflected from a first surface of the window;
    obtaining a third value indicative of a power level of a third light signal reflected from a second surface of the window; and
    determining a fourth value indicative of light transmission through the window based on the obtained first, second, and third values.

2. The method of claim 1 wherein the first and second surfaces comprise surfaces of a single-pane window.

3. The method of claim 1 wherein the first and second surfaces comprise exterior surfaces of a double-pane window.

4. The method of claim 1 wherein determining the fourth value indicative of light transmission through the window based on the obtained first, second, and third values comprises calculating the fourth value using an equation having variables for the first, second, and third values.

5. The method of claim 1 wherein determining the fourth value indicative of light transmission through the window based on the obtained first, second, and third values comprises using a lookup table to correlate stored values with the obtained first, second, and third values.

6. The method of claim 1 wherein obtaining the first value indicative of the power level of first light signal incident to the window comprises:
    splitting at least a portion of the first light signal;
    obtaining a value indicative of a power level of the portion of the light signal; and
    multiplying the obtained value indicative of the power level of the portion of the light signal with another value to obtain the first value indicative of the power level of first light signal incident to the window.

7. The method of claim 1, further comprising, if the third value indicative of the power level of the third light signal reflected from the second surface of the window is at least a magnitude greater than the first value, adjusting the obtained third value to determine the fourth value indicative of light transmission through the window.

8. The method of claim 1 wherein obtaining the first, second, and third values comprises detecting their respective light signals with a photodetector.

9. An article of manufacture, comprising:
    a machine-readable medium having stored thereon instructions to determine a resulting value indicative of light transmission through a window based on a first value indicative of a power level of a first light signal incident to the window, a second value indicative of a power level of a second light signal reflected from a first surface of the window, and a third value indicative of a power level of a third light signal reflected from a second surface of the window.

10. The article of manufacture of claim 9 wherein the instructions to determine the resulting value indicative of light transmission through the window based on the first, second, and third values include instructions to calculate the resulting value based on an equation having variables for the first, second, and third values.

11. The article of manufacture of claim 9 wherein the instructions to determine the resulting value indicative of light transmission through the window based on the first, second, and third values include instructions to use a lookup table to correlate stored values with the first, second, and third values.

12. An apparatus, comprising:
 a mount attachable to a window;
 a detector attached to the mount, the detector being movable to detect a first light signal reflected from a first surface of the window and to detect a second light signal reflected from a second surface of the window; and
 a meter unit coupled to the detector to display a value, indicative of light transmission through the window, based on the detected first and second light signals and based on a power level of an incident light signal that is incident on the first surface of the window.

13. The apparatus of claim 12, further comprising a light source attached to the mount to provide the incident light signal.

14. The apparatus of claim 13 wherein the light source comprises a laser light source.

15. The apparatus of claim 12, further comprising a processor unit coupled to the detector to obtain the value indicative of light transmission through the window and to provide the value indicative of light transmission to the meter unit to display.

16. The apparatus of claim 15 wherein the processor unit is capable to calculate the value indicative of light transmission based on an equation having variables representative of the detected first and second light signals and of the power level of an incident light signal.

17. The apparatus of claim 15, further comprising a lookup table having entries stored therein representative of power levels of the incident light signal and of the first and second light signals, wherein the processor unit is capable to correlate detected power levels of the incident light signal and of the first and second light signals with the entries stored in the lookup table to obtain the value indicative of light transmission.

18. The apparatus of claim 12 wherein the detector comprises a photodiode.

19. The apparatus of claim 12, further comprising an attachment mechanism coupled to the mount to attach the mount to the window.

20. The apparatus of claim 12 wherein the mount includes a railing, the detector capable of being moved along the railing to correspond to different positions to receive the first and second light signals.

* * * * *